United States Patent [19]

Zierenberg et al.

[11] Patent Number: 4,547,359

[45] Date of Patent: Oct. 15, 1985

[54] DIVISIBLE PHARMACEUTICAL TABLET WITH DELAYED ACTIVE INGREDIENT RELEASE

[75] Inventors: Bernd Zierenberg; Arun R. Gupte, both of Ingelheim am Rhein, Fed. Rep. of Germany

[73] Assignee: Boehringer Ingelheim KG, Ingelheim am Rhein, Fed. Rep. of Germany

[21] Appl. No.: 591,988

[22] Filed: Mar. 21, 1984

[30] Foreign Application Priority Data

Apr. 18, 1983 [DE] Fed. Rep. of Germany ....... 3314003

[51] Int. Cl.[4] .......................... A61K 9/26; A61K 9/44; A61K 31/78

[52] U.S. Cl. ........................................ 424/22; 424/15; 424/19; 424/32; 424/81

[58] Field of Search ............................. 424/15, 19–22, 424/32–33, 81

[56] References Cited

U.S. PATENT DOCUMENTS

| 2,987,445 | 6/1961 | Levesque | 424/81 |
|---|---|---|---|
| 3,087,860 | 4/1963 | Endigott | 424/81 |
| 3,390,050 | 6/1968 | Speiser | 424/81 |
| 3,520,970 | 7/1970 | Lehmann et al. | 424/25 |
| 3,608,063 | 9/1971 | Banker | 424/81 |
| 3,629,392 | 12/1971 | Banker et al. | 424/81 |
| 3,775,537 | 11/1973 | Lehmann et al. | 424/81 |
| 4,013,820 | 3/1977 | Farhadieh et al. | 424/35 |
| 4,083,969 | 4/1978 | Inoue et al. | 424/182 |
| 4,152,413 | 5/1979 | Goodnow | 424/16 |
| 4,152,414 | 5/1979 | Harris et al. | 424/16 |
| 4,152,415 | 5/1979 | Harris et al. | 424/16 |
| 4,223,006 | 9/1980 | Taskis | 424/16 |
| 4,248,855 | 2/1981 | Blank et al. | 424/81 |
| 4,343,789 | 8/1982 | Kawata et al. | 424/22 |
| 4,351,825 | 9/1982 | Sothmann et al. | 424/22 |
| 4,353,887 | 10/1982 | Hess et al. | 424/15 |
| 4,357,312 | 11/1982 | Hsieh et al. | 424/81 |
| 4,391,797 | 7/1983 | Folkman et al. | 424/19 |
| 4,404,183 | 9/1983 | Kawata et al. | 424/22 |

*Primary Examiner*—Shep K. Rose
*Attorney, Agent, or Firm*—Hammond & Littell, Weissenberger & Dippert

[57] ABSTRACT

A novel divisible delayed release pharmaceutical tablet, wherein the rate of release of active ingredient is independent of the size and nature of the total surface area, and the fragments of which have the same characteristics of release of active ingredient as the undivided tablet.

4 Claims, No Drawings

DIVISIBLE PHARMACEUTICAL TABLET WITH DELAYED ACTIVE INGREDIENT RELEASE

This invention relates to a novel divisible pharmaceutical polyacrylate-based tablet with a controlled and delayed release of the active ingredient, and to a process for the production thereof.

BACKGROUND OF THE INVENTION AND THE PRIOR ART

It is known to produce solid pharmaceutical preparations which ensure a constant release of active ingredient throughout the gastrointestinal tract over a long period of time and thus ensure a constant concentration of active ingredient in the body. These delayed release forms make it possible to reduce the number of doses of the drug to be administered daily and thus simplify the treatment plan considerably. Usually, tablets and capsules which are provided with a coating which regulates the release of active ingredient are used as delayed release forms. It has also already been proposed that delayed release forms be produced from a granulate mixture the individual components of which release the active pharmaceutical ingredient at different rates.

In addition, tablets with score lines are known which enable the tablets to be divided into partial doses in order to meet special therapeutic requirements. Divisible tablets of this kind must, in particular, satisfy the requirement of being easy and safe to divide and of ensuring precise dosage, even when broken into fragments.

One disadvantage of delayed release tablets provided with coatings is that any division of the tablet critically affects the total surface area of the tablet, that is, it increases it and some of the delaying coating is lost. As a result, the characteristics of the release of active ingredient are significantly altered, so that in many cases the fragments of the divisible delayed release tablet no longer have the property of delayed and continuous release of active ingredient or retain this property only to a very restricted extent.

In order to overcome this difficulty at least partially, an oblong delayed release tablet is proposed in German Offenlegungsschrift No. 3,030,622. This tablet consists of an elongate pressed object which is optionally provided with a coating and is formed from at least one active substance in an excipient composition which ensures a delayed, controlled release of active substance. This pressed object has to have certain characteristics with regards to its geometric dimensions.

The delayed release tablet according to German Offenlegungsschrift No. 3,030,622 has the following disadvantages:

(1) Since the rate of release of the active ingredient in this tablet is dependent on the size and nature of the total surface area, and the size and nature of the surface area are affected by any division of the tablet, such division of the tablet will inevitably affect the rate of release of the active ingredient from the fragments, even though the reduction in the delaying effect should surprisingly be less than expected.

(2) The delayed release form is tied to a certain shape and, in particular, to certain conditions regarding the geometric dimensions. Round delayed release tablets with score lines cannot be produced by the measures disclosed in this prior publication.

(3) In tablet pressing technology, experience has shown that as a result of the different conditions of compression near the score line in the pressed blanks, particularly in the case of deep notches, the tablet will tend to break next to rather than at the score line. Therefore, in this embodiment of the prior art, a poor degree of accuracy in dosage can be expected from the tablet fragments.

Finally, orally administerable pharmaceutical preparations are known wherein the active substance is embedded in a polymer. Pharmaceutical preparations of this kind are normally produced by dissolving the active ingredient together with a polymer in a solvent, then evaporating the solvent and granulating the solid mixture. Normally, the removal of the solvent and the granulation are carried out in a single operation by spraydrying.

Pharmaceutical preparations of this type are intended for the purpose of distributing the active ingredient in a finely dispersed form through the polymer and increasing the surface area of the substance which is to be dissolved, so as to accelerate and not delay the dissolving process.

OBJECTS OF THE INVENTION

It is an object of the present invention to provide a divisible delayed release tablet which is not tied to certain conditions with regard to geometric dimensions and, more particularly, wherein the rate of release of the active ingredient is independent of the size and nature of the total surface area.

It is another object of the present invention to provide a divisible delayed release tablet the fragments of which have the same characteristics of release of active ingredient as the tablet before it is divided.

Other objects and advantages of the invention will become apparent as the description thereof proceeds.

DESCRIPTION OF THE INVENTION

The above objects are achieved in accordance with the present invention by providing a divisible polyacrylate-based tablet which is characterized in that it consists essentially of a compressed composition comprising a finely divided polyacrylate material having the active ingredient incorporated therein in molecular dispersion, and conventional tablet excipients.

The polyacrylate material which is used is a copolymer of methyl and/or ethyl esters of acrylic and methacrylic acid. The copolymer should have an average molecular weight of about 800,000.

It is particularly important to use an acrylate material which has been polymerized in a certain manner. The acrylate copolymer must be produced by emulsion polymerization and should have a particle size of about 140 nm. Polyacrylates prepared by other methods, such as by solution or block polymerization, are unsuitable for purposes of the present invention. The solid substance may be recovered from the emulsion by freeze-drying or other drying methods. The particles of polymer then retain their shape and size.

A suitable starting material is the product Eudragit ® E 30 D marketed by Röhm GmbH of Darmstadt, West Germany. Naturally, it is also possible to use other polymer latices which correspond to the above-mentioned products in regard to their molecular weight and particle size and a toxicologically harmless.

In order to vary the rate of release, the copolymer may optionally contain acidic or basic groups, for instance unesterified carboxyl groups or N,N-dimethylaminoethyl ester groups. It is also possible to use polymer mixtures which contain, in addition to neutral poly(methy)acrylates, ethylene polymers with acidic or basic groups, such as poly(meth)acrylic acids of N,N-dimethylaminoethyl esters of poly(meth)acrylic acid or polyvinylpyrrolidone, which may also be present as copolymers. An example of a polymer which contains acid groups is the commercially available product Eudragit®L 100, which is a copolymer of methacrylic acid and methyl methacrylate with a molecular weight of about 250,000. A material containing basic groups is Eudragit®E 100 made by Röhm GmbH of Darmstadt, West Germany.

The pharmaceutically active ingredient may be an acidic, basic or neutral substance with a molecular weight of up to about 500. The active ingredient should be effective at low doses. In this connection, active ingredients which are normally used at a dosage level of up to 50 mg per whole tablet are particularly suitable. The weight of the individual tablets is not critical. Normally, a tablet should not weigh more than 1000 mg.

In order to ensure a delayed release of the active ingredient, the active ingredient embedded in the polyacrylate material should have diffusion coefficients of $10^{-5}$ to $10^{-7}$ cm$^2$ per hour.

The rate of release is determined not only by the diffusion coefficient but also by the particle size of the polyacrylate particles charged with molecularly dispersed active ingredient and by the distribution of the particle size. The particle size is advantageously between 10 and 500 μm. Smaller particle sizes normally give a more rapid rate of release, which means that the rate of release can be varied by fractionation of the particle sizes. Conversely, different particle size fractions can be mixed together so as to obtain suitable rates of release.

The rate of release can also be controlled, when using acidic or basic active ingredients, by using a polyacrylate material which contains acidic or basic groups. The rate of release can be reduced by salt formation between a basic active ingredient and acidic groups contained in the polyacrylate material, or between an acidic active ingredient and basic groups contained in the polyacrylate material.

Finally, the rate of release can be varied by the use of substances which affect diffusion, such as polyvinylpyrrolidone or cellulose esters.

The invention further relates to a process for producing the divisible tablet with delayed release of active ingredient described above.

The finely divided polyacrylate material with the active ingredient in molecular dispersion in the polymer, which is required for tablet making, must be produced in a special way, and in a separate step. We have found, in particular, that attempts to granulate a solution of the pharmaceutically active ingredient and polyacrylate in an organic solvent directly with a tablet-making excipient are unsuccessful. The rate of release of the tablets produced from this granulate was about 90% of the available active ingredient within 15 minutes. This finding shows that in the granulating process followed by the drying process, the pharmaceutically active ingredient and the polymer carrier diffused too easily over the available surface of the tablet-making excipient; in other words, the pharmaceutically active ingredient is not incorporated or bound in the polymer.

The divisible tablet with delayed release of active ingredient pursuant to the present invention is produced by dissolving the pharmaceutically active ingredient together with the polyacrylate material in an organic solvent, evaporating the solvent, grinding the residual solid polyacrylate which contains the active ingredient at a temperature below the glass temperature, compounding the active ingredient-containing polyacrylate powder with conventional tablet-making excipients, and compressing the resulting granulate to form tablets which may optionally comprise a score line.

Suitable solvents for the solution containing the active ingredient and polyacrylate include, in particular, readily volatilizable solvents such as methanol, ethanol, acetone, methylene chloride, methyl and ethyl acetates, methyl and ethyl acetoacetates or ethers such as tetrahydrofuran or dioxane, or dimethylsulfoxide or mixtures of these solvents.

In order to ensure rapid evaporation at as low a temperature as possible, the solution containing the active ingredient and polyacrylate may be poured into flat molds, such as dishes, so that a relatively thin layer thickness is obtained. Then, after drying, a film is obtained the longitudinal and thickness dimensions of which depend on the evaporation vessel which is used.

The polyacrylate material obtained in this way having the active ingredient in a molecular dispersion incorporated therein has a certain viscosity and inherent thickness and cannot be ground as such. In order to grind up the polymer, it has to be brought to a temperature below the glass temperature, that is, it must be cooled. This can be done, for example, with solid or liquid carbon dioxide, liquid air or liquid nitrogen or other liquefied inert gases. The polymer is thus made brittle and can then be broken up. The ground material has a tendency to coalesce again when heated to room temperature. It is therefore advisable to add a finely divided inert filler to the ground material during the grinding process; this filler may be, for example, lactose, finely divided silica, magnesium stearate or similar finely divided lubricants. The mass ratio of active ingredient-containing polyacrylate to finely divided filler may vary within wide limits and may be from about 10:1 to 1:4.

In this way, a free-flowing powder is obtained which can be compressed in a further step with the usual tablet-making excipients in a normal tablet-making press with a scoring device to produce a divisible tablet. Tablet-making excipients include, for example, binders, inert fillers, lubricants as well as disintegrants.

The following examples illustrate the present invention and will enable others skilled in the art to understand it more completely. It should be understood, however, that the invention is not limited solely to the particular examples given below.

EXAMPLE 1

40 g of Eudragit®E 30 D (freeze-dried), 5 g of clonidine base and 455 g of acetone were combined in a suitable vessel, and the mixture was stirred until a completely clear solution was obtained. The solution thus produced was transferred into a dish from which the solvent could evaporate at room temperature. The residual film charged with active ingredient was cooled to about −40° C. using dry ice and was ground in batches together with lactose in a ratio of 9:1 in a mill with a rotating blade, while cooling. A free-flowing powder was obtained wherein the clonidine-containing polacrylate was present in a particle size distribution of about 10 to 500 μm.

The mixture of clonidine and lactose embedded as a molecular dispersion in polyacrylate particles obtained as described above was then granulated in the next step with another portion of lactose and polyvinylpyrrolidone, using water as the granulation liquid, and was then compressed, with the addition of corn starch, colloidal silicic acid and magnesium stearate as tablet-making excipients, in an eccentric press with a scoring device to form tablets weighing a total of 180.0 mg. No difficulties were encountered in these steps. The exact composition and some technical data relating to the finished tablets are give below:

TABLE 1

| Ingredients | Amount in mg/tablet |
|---|---|
| Polyacrylate carrier* | 2.50 |
| Lactose | 158.75 |
| Polyvinylpyrrolidone | 3.75 |
| Corn starch | 13.50 |
| Colloidal silicic acid | 1.00 |
| Magnesium stearate | 0.40 |
| | 180.00 |

| * Polyacrylate carrier | mg/2.50 mg of carrier |
|---|---|
| Clonidine base | 0.25 |
| Polyacrylate | 2.00 |
| Lactose | 0.25 |
| Breaking strength: 2.16 N/mm² | |
| Disintegration: 61 sec. | |

The in vitro release test of the tablets was carried out in a USP apparatus at 37° C.; 4 tablets were tested in each container. The conversion from gastric to intestinal juice took place after one hour, and the clonidine base released was analyzed by high pressure liquid chromatography. After the disintegration of the tablet, apart from the water-insoluble tablet-making excipients, there also remained the polyacrylate particles charged with the drug out of which the clonidine base diffused throughout the entire observation period.

| | Release values: |
|---|---|
| Time in hours | Quantity of clonidine released in % |
| 0.25 | 29.1 |
| 1 | 39.5 |
| 2 | 54.9 |
| 4 | 60.8 |
| 6 | 68.3 |

EXAMPLE 2

38 g of Eudragit ®E 30 D (freeze-dried) were dissolved in 430 ml of acetone in a suitable vessel and then combined with the active substance solution consisting of 2 g of etilefrin base and 80 ml of methanol. The clear solution thus obtained was transferred into a dish, and the solvent was evaporated at room temperature; a clear film charged with active ingredient was obtained. The film was cooled to about −40° C. with dry ice and ground with lactose in a mass ratio of 10:1 in a mill and then processed to form tablets.

| | Release values: |
|---|---|
| Time in hours | Quantity released in % |
| 0.25 | 10.9 |
| 1 | 22.9 |
| 2 | 37.0 |
| 4 | 46.0 |
| 6 | 51.5 |

The in vitro release test was carried out in a USP apparatus as in Example 1. Analytical determination of the active ingredient released was carried out by UV measurement.

EXAMPLE 3

100 g of Eudragit ®E 30 D (freeze-dried), 2.5 g of clonidine base and 800 g of acetone were placed in a suitable vesel and stirred until a clear solution was formed. In a second vessel, 25 g of Eudragit ®L 100 were dissolved in 500 g of ethanol and added to the above solution while stirring, thereby forming a milky, white solution. After the mixture of solvents had been evaporated in a suitable dish, a slightly milky film was obtained which was cooled with dry ice to about −40° C., then ground and finally processed to form tablets.

| | Release values: |
|---|---|
| Time in hours | Quantity of clonidine released in % |
| 0.25 | 11.1 |
| 1 | 17.1 |
| 2 | 37.2 |
| 4 | 41.5 |
| 6 | 43.5 |

The release values were determined as described in Example 1.

EXAMPLE 4

50 g of Eudragit ®E 30 D (freeze-dried), 2.33 g of clonidine base and 5.82 g of polyvinylpyrrolidone were placed in a suitable vessel, mixed with 1000 ml of acetone and dissolved while stirring. After the solution had been formed, the solvent was evaporated in an open dish, the film obtained was cooled with dry ice to about −40° C., then ground and processed to form tablets.

The release curve gave the following sequence of values in percent.

| Time in hours | Quantity of clonidine released in % |
|---|---|
| 0.25 | 12.6 |
| 1 | 24.7 |
| 2 | 33.3 |
| 4 | 44.2 |
| 6 | 52.5 |

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A pharmaceutical delayed active ingredient release tablet wherein the rate of release of active ingredient from any fragment thereof is the same and independent of the size and nature of the total surface area, consisting of a compressed tablet-making composition comprising finely divided active ingredient-containing emulsion-polymerized polyacrylate material having a particle size between 10 and 500 microns ground below the glass temperature without the excipients, conventional tablet-making excipients and active ingredient with a molecular weight of up to about 500 and a diffusion coefficient of about $10^{-5}$ to $10^{-7}$ cm$^2$/hr molecularly dispersed in said polyacrylate material.

2. A pharmaceutical tablet of claim 1, where said polyacrylate material is a copolymer of methyl and/or ethyl esters of acrylic and methacrylic acid having an average molecular weight of about 800,000.

3. A pharmaceutical tablet of claim 2, where ethylene polymers with acidic or basic groups are admixed with the polyacrylate material.

4. A pharmaceutical tablet of claim 1, where said active ingredient is present in an amount up to 50 milligrams.

* * * * *

UNITED STATES PATENT AND TRADEMARK OFFICE
CERTIFICATE OF CORRECTION

PATENT NO. : 4,547,359

DATED : Oct. 15, 1985

INVENTOR(S) : BERND ZIERENBERG ET AL.

It is certified that error appears in the above-identified patent and that said Letters Patent is hereby corrected as shown below:

Column 5, line 2: "ρm" should read -- μm --.

Column 5, line 14: "give" should read -- given --.

Column 6, line 16: "vesel" should read -- vessel --.

Signed and Sealed this

Fourteenth Day of January 1986

[SEAL]

Attest:

Attesting Officer

DONALD J. QUIGG

Commissioner of Patents and Trademarks